US011318072B2

(12) United States Patent
Pierre et al.

(10) Patent No.: US 11,318,072 B2
(45) Date of Patent: *May 3, 2022

(54) MATT-EFFECT COMPOSITION COMPRISING HYDROPHOBIC AEROGEL PARTICLES AND SILICONE ELASTOMER PARTICLES

(71) Applicant: L'OREAL, Paris (FR)

(72) Inventors: Patricia Pierre, Antony (FR); Eric Lheureux, Montgeron (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/543,954

(22) Filed: Aug. 19, 2019

(65) Prior Publication Data
US 2020/0069537 A1 Mar. 5, 2020

Related U.S. Application Data

(63) Continuation of application No. 14/409,023, filed as application No. PCT/EP2013/063083 on Jun. 21, 2013, now abandoned.

(60) Provisional application No. 61/692,721, filed on Aug. 24, 2012.

(30) Foreign Application Priority Data

Jun. 21, 2012 (FR) ..................... 1255839

(51) Int. Cl.
A61K 8/02 (2006.01)
A61Q 19/00 (2006.01)
A61K 8/25 (2006.01)
A61K 8/58 (2006.01)
A61K 8/895 (2006.01)
A61K 8/81 (2006.01)

(52) U.S. Cl.
CPC .......... *A61K 8/0245* (2013.01); *A61K 8/0241* (2013.01); *A61K 8/0279* (2013.01); *A61K 8/25* (2013.01); *A61K 8/585* (2013.01); *A61K 8/8152* (2013.01); *A61K 8/895* (2013.01); *A61Q 19/00* (2013.01); *A61Q 19/008* (2013.01); *A61K 2800/412* (2013.01); *A61K 2800/592* (2013.01); *A61K 2800/60* (2013.01)

(58) Field of Classification Search
None
See application file for complete search history.

(56) References Cited

U.S. PATENT DOCUMENTS 5,914,102 A 6/1999 Fowler et al.
2001/0026811 A1 10/2001 Rouquet et al.
2002/0018790 A1* 2/2002 Vatter ............... A61Q 1/02 424/401
2004/0265347 A1 12/2004 Auguste et al.
2005/0187128 A1 8/2005 Martin et al.
2005/0191328 A1* 9/2005 Taniguchi ............... A61K 8/24 424/401
2006/0034788 A1 2/2006 Horino et al.
2006/0039938 A1 2/2006 Josse
2006/0135397 A1 6/2006 Bissey-Beugras
2008/0119527 A1 5/2008 Baldo
2009/0247648 A1 10/2009 Zhao
2010/0256100 A1 10/2010 Quedville

FOREIGN PATENT DOCUMENTS

| DE | 102008017031 A1 | 12/2008 |
|---|---|---|
| EP | 0765656 | 4/1997 |
| EP | 1473018 A1 | 11/2004 |
| EP | 1627624 A1 | 2/2006 |
| FR | 2869796 A1 | 11/2005 |
| FR | 2952303 A1 | 5/2011 |
| FR | 2960434 A1 | 12/2011 |
| GB | 2423250 A | 8/2006 |
| JP | H11-246381 | 9/1999 |
| JP | 2003-137760 A | 5/2003 |
| JP | T-2004-529173 | 9/2004 |
| JP | 2005-97246 A | 4/2005 |
| JP | 2006-160714 A | 6/2006 |
| JP | 2006-56889 A | 9/2007 |
| WO | WO-9704737 A1 | 2/1997 |
| WO | WO-02/092046 | 11/2002 |
| WO | WO-2009/098839 | 8/2009 |
| WO | WO-2009120602 A1 | 10/2009 |
| WO | WO-2012085855 A2 | 6/2012 |

OTHER PUBLICATIONS

Dow Corning: "Marzipan Souffle: Make up base, Sebum Control", Nov. 18, 2006, pp. 1-2.
Dow Corning: "Dow Corning VM-2270 Aerogel Fine Particles", Apr. 2009, pp. 1-5.
"Silica Silylate Aerogel for Cosmetic Applications", IP.com Journal, No. IPCOM000133571D, Jan. 30, 2006.
"High-performance mico-sphere fine silica Sunsphere", Dec. 1, 2005, pp. 1-12 (URL:http://www/agc-si.com/en/product/pdf/SUNSPHERE.pdf).
Dow Corning, Control the Shine for Men, Formulation 01140.
Dow Corning, Oil-in-Water Skin Cream, 2010, p. 1-2.

\* cited by examiner

Primary Examiner — Jennifer A Berrios
(74) Attorney, Agent, or Firm — Polsinelli PC

(57) ABSTRACT

The present invention relates to a cosmetic and/or dermatological composition comprising, in a physiologically acceptable medium:
a) at least some hydrophobic aerogel particles,
b) at least some silicone elastomer particles,
c) at least one particle that absorbs sebum.
The invention also relates to a process for making the skin matt and/or for reducing its shine.

13 Claims, No Drawings

MATT-EFFECT COMPOSITION COMPRISING HYDROPHOBIC AEROGEL PARTICLES AND SILICONE ELASTOMER PARTICLES

CROSS REFERENCE TO RELATED APPLICATIONS

This application is a Continuation of U.S. application Ser. No. 14/409,023 filed on Jun. 21, 2013, which is the National Phase filing under 35 U.S.C. § 371 of PCT/EP2013/063083 filed on Jun. 21, 2013; which application in turn claims priority to Application No. 1255839 filed in France on Jun. 21, 2012, and which application also claims the benefit of U.S. Provisional Application No. 61/692,721 filed on Aug. 24, 2012. The entire contents of each application are hereby incorporated by reference.

The present invention relates to the field of caring for and/or making up keratin materials, and in particular the skin.

The invention relates to a cosmetic and/or dermatological composition comprising, in a physiologically acceptable medium, at least some hydrophobic aerogel particles, some silicone elastomer particles and at least one particle that absorbs sebum.

The invention also relates to a process for caring for and/or making up the skin, comprising the topical application of the composition to the skin.

The invention also relates to a cosmetic process for making the skin matt and/or for reducing its shine, comprising the topical application to the said skin of the above-mentioned composition.

Shiny skin, generally associated with a substantial secretion of sebum, is a problem essentially affecting adolescents, but which may also appear in adulthood as a result especially of an overproduction of androgens, or as a result of external factors such as pollution. Shiny skin may also be associated with sweat resulting from physical activity or weather conditions. Shiny skin may be due to the combination of both these phenomena (sebum and sweat).

Obtaining a matt effect on the skin is highly desired by users who have combination or oily skin, and also for cosmetic compositions that are intended to be used in hot and humid climates. The reflections caused by excess sebum and/or sweat on the surface of the skin are, indeed, generally considered unattractive.

Shiny skin also generally gives rise to poorer makeup staying power, which thus has a tendency to become degraded in the course of the day.

An effective means of quickly reducing areas of unattractive shine consists in using "soft-focus" blurring-effect fillers. Using fillers that absorb sebum and perspiration is also a means for adding and/or prolonging mattness over time.

It is known practice to use perlite (FR 2 881 643), fumed fillers (EP 1 637 186) or fibres as mattifying agents. However, these fillers may afford adverse results, especially clumps on the skin and/or a sensation of unclean skin. It is thus sought to limit the filler content.

The need remains for mattifying cosmetic compositions which have good cosmetic properties, and which in particular afford an efficient (strong), immediate and/or long-lasting mattifying effect.

The Applicant has discovered that this need could be met by combining several specific fillers and especially a) at least some hydrophobic aerogel particles, b) some silicone elastomer particles different than the particles a) and c), and c) at least some mattifying particles different than the particles a) and b).

The composition thus obtained makes it possible to improve skin mattness in a lasting manner. The skin is thus rendered matt in a long-lasting manner. What is more, the performance of the combination of the three types of particles is greater than that of each of the particles taken in isolation.

The compositions according to the invention can also make it possible to reduce the perception of skin defects at the surface of the skin and in particular to mask wrinkles and pores and/or to hide coloured defects of the skin, namely red blotches or blemishes.

Moreover, the compositions according to the invention are fresh upon application and spread easily.

A subject of the present invention is thus a cosmetic and/or dermatological composition comprising, in a physiologically acceptable medium:
  a) at least some hydrophobic aerogel particles
  b) at least some silicone elastomer particles different than the particles c), and
  c) at least one particle that absorbs sebum different than the particles a) and b),
  the said composition comprising at least one aqueous phase.

The constituents of the composition according to the invention will now be described in greater detail.

Hydrophobic Aerogels:

Aerogels are ultra-light porous materials. The first aerogels were made by Kristler in 1932. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. Other types of drying also make it possible to obtain porous materials starting from gel, namely cryodesiccation, which consists in solidifying the gel at low temperature and in then subliming the solvent, and drying by evaporation. The materials thus obtained are referred to respectively as cryogels and xerogels. The sol-gel process and the various drying operations are described in detail in Brinker C. J. and Scherer G. W., Sol-Gel Science, New York: Academic Press, 1990.

The aerogel particles in accordance with the present invention are hydrophobic aerogel particles.

The term "hydrophobic aerogel particle" means any particle of the aerogel type having a water absorption capacity at the wet point of less than 0.1 ml/g, i.e. less than 10 g of water per 100 g of particle.

The wet point corresponds to the amount of water that needs to be added to 1 g of particle in order to obtain a homogeneous paste. This method is derived directly from the method for determining the oil uptake of a powder as described in standard NF T 30-022. The measurements are taken in the same manner by means of the wet point and the flow point, which have, respectively, the following definitions:

wet point: weight expressed in grams per 100 g of product corresponding to the production of a homogeneous paste during the addition of a solvent to a powder.

The wet point is measured according to the following protocol:

Equipment used:
  Glass plate (25×25 mm)
  Spatula (wooden shaft and metal part, 15×2.7 mm)
  Silk-bristled brush Balance The glass plate is placed on the balance and 1 g of aerogel is weighed out. The beaker containing the solvent and the liquid sampling pipette is placed on the balance. The solvent is gradually added to the powder, the whole being regularly blended (every 3 to 4 drops) with the spatula. The mass of solvent required to reach the wet point is noted. The average of three tests will be determined.

The hydrophobic aerogels used according to the present invention may be organic, inorganic or organic-inorganic hybrid aerogels.

The organic aerogels may be based on resins from among the following: polyurethanes, resorcinol-formaldehyde, polyfurfuranol, cresol-formaldehyde, phenol-furfuranol, polybutadiene, melamine-formaldehyde, phenol-furfural, polyimides, polyacrylates, polymethacrylates, polyolefins, polystyrenes, polyacrylonitriles, phenol-formaldehyde, polyvinyl alcohol, dialdehydes, polycyanides, epoxys, celluloses, cellulose derivatives, chitosan, agar, agarose, alginate, starches, and mixtures thereof.

Aerogels based on organic-inorganic hybrids, for example silica-PMMA, silica-chitosan and silica-polyether, are also envisaged. Patent applications US 2005/0 192 366 and WO 2007/126 410 describe such organic-inorganic hybrid materials.

The hydrophobic aerogel particles used in the present invention have a specific surface area per unit of mass ($S_M$) ranging from 200 to 1500 $m^2/g$, preferably from 600 to 1200 $m^2/g$ and better still from 600 to 800 $m^2/g$, and a size, expressed as the volume-mean diameter (D[0.5]), of less than 1500 μm and preferably ranging from 1 to 30 μm, more preferably from 5 to 25 μm, better still from 5 to 20 μm and even better still from 5 to 15 μm.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of the aerogel particles according to the invention can be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles", Chapters 9 and 10, Wiley, New York, 1957.

According to an advantageous embodiment, the hydrophobic aerogel particles used in the present invention have a specific surface area per unit of mass ($S_M$) ranging from 600 to 800 $m^2/g$ and a size, expressed as the volume-mean diameter (D[0.5]), ranging from 5 to 20 μm and better still from 5 to 15 μm.

The hydrophobic aerogel particles used in the present invention may advantageously have a tapped density p ranging from 0.02 $g/cm^3$ to 0.10 $g/cm^3$ and preferably from 0.03 $g/cm^3$ to 0.08 $g/cm^3$.

In the context of the present invention, this density may be assessed according to the following protocol, known as the tapped density protocol:

40 g of powder are poured into a measuring cylinder; the measuring cylinder is then placed on the Stay 2003 machine from Stampf Volumeter; the measuring cylinder is subsequently subjected to a series of 2500 tapping actions (this operation is repeated until the difference in volume between 2 consecutive tests is less than 2%); and then the final volume Vf of tapped powder is measured directly on the measuring cylinder. The tapped density is determined by the ratio m/Vf, in this instance 40/Vf (Vf being expressed in $cm^3$ and m in g).

According to one embodiment, the hydrophobic aerogel particles used in the present invention have a specific surface area per unit of volume $S_V$ ranging from 5 to 60 $m^2/cm^3$, preferably from 10 to 50 $m^2/cm^3$ and better still from 15 to 40 $m^2/cm^3$.

The specific surface area per unit of volume is given by the relationship: $S_V = S_M \cdot \rho$ where $\rho$ is the tapped density expressed in $g/cm^3$ and $S_M$ is the specific surface area per unit of mass expressed in $m^2/g$, as defined above.

Preferably, the hydrophobic aerogel particles according to the invention have an oil-absorbing capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil that needs to be added to 100 g of particles in order to obtain a homogeneous paste.

It is measured according to the "wet point" method or method for determining the oil uptake of a powder as described in standard NF T 30-022. It corresponds to the amount of oil adsorbed onto the available surface of the powder and/or absorbed by the powder by measurement of the wet point, described below: An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added one drop at a time and the mixture is then triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

According to a particular embodiment, the aerogel particles used are inorganic and are more particularly hydrophobic silica aerogels having the properties stated previously.

Silica aerogels are porous materials obtained by replacing (especially by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York: Academic Press, 1990.

The hydrophobic silica aerogels used according to the present invention are preferably silylated silica aerogels (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will in particular be made of the hydrophobic silica aerogel particles that have been surface-modified with trimethylsilyl groups.

As hydrophobic silica aerogels that may be used in the invention, examples that may be mentioned include the aerogel sold under the name VM-2260 (INCI name: Silica silylate) by Dow Corning, the particles of which have a mean size of about 1000 microns and a specific surface area per unit of mass ranging from 600 to 800 $m^2/g$.

Mention may also be made of the aerogels sold by Cabot under the references Aerogel TLD 201, Aerogel OGD 201 and Aerogel TLD 203, Enova® Aerogel MT 1100 and Enova Aerogel MT 1200.

Use will more particularly be made of the aerogel sold under the name VM-2270 (INCI name: Silica silylate) by Dow Corning, the particles of which have a mean size ranging from 5-15 microns and a specific surface area per unit of mass ranging from 600 to 800 $m^2/g$.

Use will also be made of the aerogel sold under the name Enova® Aerogel MT 1100 (INCI name: Silica silylate) by Cabot, the particles of which have a mean size ranging from 2-25 microns and a specific surface area per unit of mass ranging from 600 to 800 $m^2/g$.

The hydrophobic aerogel particles represent from 0.1% to 30% by weight, preferably from 0.5% to 20% by weight, better still from 1% to 10% by weight and more preferably from 1.5% to 5% by weight relative to the total weight of the composition.

Silicone Elastomer Particles

The composition of the invention comprises at least one organopolysiloxane elastomer, preferably at least partially crosslinked.

The term "elastomer" is understood to mean a deformable, flexible, solid material having viscoelastic properties and especially the consistency of a sponge or of a flexible sphere. Its modulus of elasticity is such that this material withstands deformation and has a limited ability to extend and to contract. This material is capable of regaining its original shape after stretching. This elastomer is formed from high-molecular-weight polymer chains, the mobility of which is limited by a uniform network of crosslinking points.

The organopolysiloxane elastomers used in the composition according to the invention are preferably partially or completely crosslinked. They are provided in the form of particles. In particular, the organopolysiloxane elastomer particles have a size ranging from 0.1 to 500 µm, preferably from 3 to 200 µm and better still from 3 to 50 µm. These particles can have any shape and can, for example, be spherical, flat or amorphous.

When they are included in an oil phase, these organopolysiloxane elastomers transform, according to the level of oil phase used, into a product with a spongy appearance when they are used in the presence of low contents in the oil phase, or into a homogeneous gel in the presence of higher quantities of oil phase. The oil phase can be completely or partially gelled by these elastomers.

Accordingly, the elastomers of the invention may be conveyed in the form of an anhydrous gel constituted of an organopolysiloxane elastomer and an oil phase. The oil phase used while manufacturing the anhydrous organopolysiloxane elastomer gel contains one or more oils that are liquid at room temperature (25° C.) chosen from hydrocarbon-based oils and/or silicone oils. Advantageously, the oil phase is a silicone-based liquid phase, containing one or more oils chosen from polydimethylsiloxanes with straight or cyclic chains, which are liquid at room temperature, optionally containing an alkyl or aryl chain that is pendent or at the chain end, the alkyl chain having from 1 to 6 carbon atoms.

The organopolysiloxane elastomers used according to the invention may be chosen from crosslinked polymers described in application EP-A-0295886 and from those described in patent U.S. Pat. No. 5,266,321.

According to one embodiment, the organopolysiloxane elastomers used according to the invention may be obtained by an addition and crosslinking reaction, in the presence of a catalyst, preferably a platinum type catalyst, of at least:
  (a) an organopolysiloxane having two vinyl groups in the α-ω position of the silicone chain per molecule; and
  (b) an organopolysiloxane having at least two hydrogen atoms bound to a silicon atom per molecule.

The first organopolysiloxane (i) is chosen from polydimethylsiloxanes; this is preferably a α-ω-dimethylvinyl polydimethylsiloxane.

The organopolysiloxane is preferably in a gel obtained according to the following steps:
  (a) mixing the first and second organopolysiloxanes (i) and (ii);
  (b) adding an oil phase to the mixture from step (a);
  (c) polymerizing the first and second organopolysiloxanes (i) and (ii) in the oil phase in the presence of a catalyst, preferably a platinum catalyst.

According to one embodiment, the crosslinked organopolysiloxane may be obtained by a polymeric addition reaction of an organohydrogen polysiloxane having formula (I) with an organopolysiloxane having formula (II) and/or an unsaturated hydrocarbon chain having formula (Ill).

According to a variant, the crosslinked organopolysiloxane is obtained by a polymeric reaction of an organohydrogen polysiloxane having formula (I) with an organopolysiloxane having formula (II).

Organohydrogen Polysiloxane Having Formula (I)

The organohydrogen polysiloxane having formula (I) comprises at least one structural unit chosen from the group composed of a $SiO_2$ unit, a $HSiO_{1.5}$ unit, a $RSiO_{1.5}$ unit, a RHSiO unit, a $R_2SiO$ unit, a $R_3SiO_{0.5}$ unit and a $R_2HSiO_{0.5}$ unit, the R group being in these units a monovalent hydrocarbon chain containing from 1 to 16 carbon atoms that may be substituted or unsubstituted but being distinct from an unsaturated aliphatic group, and having on average at least 1.5 hydrogen atoms bound to a silicon atom.

The R group in the organohydrogen polysiloxane having formula (I) may be an alkyl group containing from 1 to 16, preferably from 10 to 16 carbon atoms. This R group may for example be a methyl group, an ethyl group, a propyl group, a lauryl group, a myristyl group or a palmityl group.

The R group in the organohydrogen polysiloxane having formula (I) may also be an aryl group such as a phenyl or tolyl group.

The R group still in the organohydrogen polysiloxane having formula (I) may also be a monovalent hydrocarbon chain comprising a cycloalkyl group such as cyclohexyl or a hydrocarbon chain substituted by one, two or more groups chosen from a halogen atom such as chlorine, bromine, fluorine and a cyano group, for example an a-trifluoropropyl or chloromethyl group.

Specifically, it is preferred that the R group represents at least 30 molar % of methyl group and from 5 to 50 molar %, preferably from 10 to 40 molar % of hydrocarbon chain containing from 10 to 16 carbon atoms.

The hydrocarbon chain can then advantageously contain at least one lauryl group, or the majority of the R groups can be lauryl groups.

The organohydrogen polysiloxane having formula (I) may be straight, branched or cyclic.

The organohydrogen polysiloxane having formula (I) preferably contains from 2 to 50 and even more preferably from 2 to 10 hydrogen atoms bound to a silicon atom (Si—H). The content of hydrogen atoms bound to a silicon atom in this compound having formula (I) varies conventionally from 0.5 to 50 molar %, and even more preferably from 1 to 20 molar % compared with the total sum of the hydrogen atoms and all the organic groups bound to a silicon atom.

Organopolysiloxane Having Formula (II)

The organopolysiloxane having formula (II) comprises at least one structural unit chosen from the group composed of a $SiO_2$ unit, a $(CH_2=CH)SiO_{1.5}$ unit, a $RSiO_{1.5}$ unit, a $R(CH_2=CH)SiO$ unit, a $R_2SiO$ unit, a $R_3SiO_{0.5}$ unit and a $R_2(CH_2=CH)SiO_{0.5}$ unit, the R group being as defined in formula (I) and having on average at least 1.5 vinyl groups bound to a silicon atom.

This compound contains preferably from 2 to 50 vinyl groups bound to a silicon atom. The average number of vinyl groups bound to a silicon atom varies preferably from 2 to 10, and even more preferably from 2 to 5.

Preferably, at least 30 molar % of the R groups are methyl groups and 5 to 50 molar %, preferably 10 to 40 molar % of the R groups are a hydrocarbon chain containing from 10 to 16 carbon atoms.

The organopolysiloxane having formula (II) may be straight, branched or cyclic. The vinyl group content in the compound having formula (II) varies preferably between 0.5 and 50 molar %, even more preferably from 1 to 20 molar % with respect to all the organic groups bound to a silicon atom.

Optional Unsaturated Hydrocarbon Chain Having Formula (III)

The unsaturated hydrocarbon chain having formula (III) meets the following formula:

$$C_mH_{2m-1}(CH_2)_xC_mH_{2m-1}$$

in which
m is an integer ranging from 2 to 6, and
x is an integer at least equal to 1.
x is preferably an integer ranging from 1 to 20.

As examples of this compound having formula (III), pentadiene, hexadiene, heptadiene, octadiene, pentadecadiene, heptadecadiene and pentatriacontadiene may be mentioned.

Polymeric addition reactions are described in detail in document US 2004/0234477.

Among crosslinked organopolysiloxanes, crosslinked polyalkyl dimethylsiloxanes are preferred. Polyalkyl dimethylsiloxane is understood to mean a straight organopolysiloxane having formula (IV)

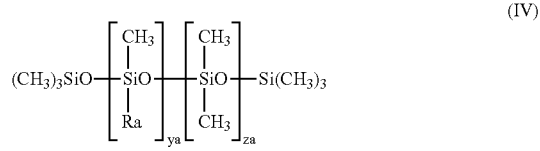

containing grafts bound monovalently or divalently having formula (V)

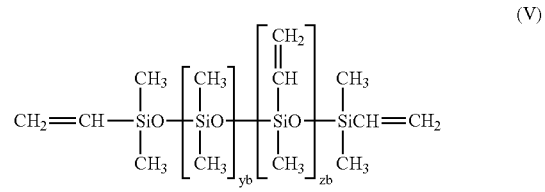

in which:
Ra is an alkyl group containing from 10 to 16 carbon atoms, and may be in a preferred manner a lauryl group,
ya is an integer ranging from 1 to 100,
za is an integer ranging from 1 to 100,
yb is an integer ranging from 1 to 100,
zb is an integer ranging from 1 to 100.

"Divalently bound" is understood to mean bound to two distinct organopolysiloxanes having formula (IV). In other words, this is a bridge between two straight chains as defined by formula (IV).

The organopolysiloxane elastomers used in the composition of the invention may for example be those sold under the names KSG 6 by Shin-Etsu; Trefil E-505C or Trefil E-506C by Dow-Corning; Gransil (SR-CYC, SR DMF10, SR-DC556) by Grant Industries, or those sold in the form of gels that are already constituted: KSG 15, KSG 16, KSG 17, KSG 18, KSG 26A, KSG 26B, KSG 41, KSG 42, KSG 43, KSG 44 by Shin-Etsu; Gransil SR SCYC gel, Gransil SR DMF 10 gel, Gransil SR DC556 gel by Grant Industries; 1229-02-167 and 1229-02-168 by General Electric. A mixture of silicone elastomers may also be used, and especially a mixture of these commercial products.

Preferably, an organopolysiloxane elastomer will be used that is sold in a form such that it is conveyed in a silicone-containing oil.

The organopolysiloxane elastomer used in the composition of the invention may also be in the form of an anhydrous gel, and especially of an anhydrous gel formed of non-spherical particles of organopolysiloxane elastomer.

The silicone elastomers are especially elastomeric partially or completely crosslinked organopolysiloxanes, having a three-dimensional structure, such as those sold under the names KSG6®, KSG16® and KSG18® by SHIN-ETSU, Trefil E-505C® and Trefil E-506C® by DOW-CORNING, Gransil SR-CYC®, SR DMF10®, SR-DC556®, SR 5CYC gel®, SR DMF 10 gel® and SR DC 556 gel® by GRANT INDUSTRIES, SF 1204® and JK 113® by GENERAL ELECTRIC.

Silicone elastomer powders that may be mentioned include the powders sold under the names "Trefil® Powder E-505C" and "Trefil® Powder E-506C" by DOW CORNING.

As silicone powder, gum beads of crosslinked polydimethylsiloxane coated with silsesquioxane resin may be mentioned, especially sold under the name KSP100 by Shin Etsu, silicone resin powders in the form of rugby balls such as especially the product sold under the name NLK-602 by TAKEMOTO.

Preferably, the silicone elastomer particles have a number-average size of between 50 nm and 350 microns, better still between 100 nm and 100 microns and even more preferentially between 0.5 and 100 microns.

The silicone elastomer particles are present in the composition according to the invention in a content ranging from 0.01% to 30% by weight, preferably ranging from 0.05% to 20% by weight, better still ranging from 0.10% to 10% by weight and more preferably ranging from 0.20% to 5% by weight relative to the total weight of the composition.

Particles that Absorb Sebum

The composition according to the invention comprises particles that absorb sebum, particularly having a different sebum uptake than the 2 types of particles a) and b).

Advantageously, the sebum-absorbing particles have a sebum uptake of greater than or equal to 10 ml/100 g, especially greater than or equal to 20 ml/100 g and in particular greater than or equal to 30 ml/100 g.

The term "sebum-absorbing particle" means a powder that is capable of absorbing and/or adsorbing sebum. Generally, this type of particle is in the form of a powder of particles having a sebum uptake.

The sebum uptake corresponds to the amount of sebum absorbed and/or adsorbed by the particle. It is measured according to the wet point method described below.

Advantageously, the sebum-absorbing particle may have a BET specific surface area of greater than or equal to 200 $m^2/g$, preferably greater than 350 $m^2/g$ and preferentially greater than 500 $m^2/g$, and especially less than 2000 $m^2/g$.

The BET specific surface area is determined according to the BET (Brunauer-Emmett-Teller) method described in The Journal of the American Chemical Society, Vol. 60, page 309, February 1938 and corresponding to the international standard ISO 5794/1 (appendix D). The BET specific surface area corresponds to the total specific surface area (thus including micropores) of the particle and especially of the powder.

The sebum-absorbing particles may be an inorganic powder or an organic powder. The particle or particles of one or more inorganic compounds used in the cosmetic composition may have different shapes, for example spheres, full or hollow, glitter, needles or platelets and preferably they are approximately spherical.

More precisely, the sebum-absorbing particles may be chosen from:

silica powders,
polyamide (Nylon®) powders,
powders of acrylic polymers, especially of polymethyl methacrylate, poly(methyl methacrylate/ethylene glycol di methacrylate), poly(allyl methacrylate/ethylene glycol dimethacrylate), ethylene glycol dimethacrylate/lauryl methacrylate copolymer,
powders of silicone elastomer, obtained especially by polymerization of organopolysiloxane containing at least two hydrogen atoms each bonded to a silicon atom and of an organopolysiloxane comprising at least two ethylenically unsaturated groups (especially two vinyl groups) in the presence of a platinum catalyst,
talc,
boron nitride,
clays,
a mixture thereof.

The sebum-absorbing particle may be a powder coated with a hydrophobic treatment agent.

The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, waxes, and mixtures thereof. The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The term "alkyl" mentioned in the compounds mentioned above especially denotes an alkyl group containing from 1 to 30 carbon atoms and preferably containing from 5 to 16 carbon atoms.

As non-limiting illustrations of sebum-absorbing particles according to the invention, mention may be made most particularly of the particles below.

Silicas that can be used may be natural and untreated. Mention may thus be made of the silicas provided under the names Sillitin N85, Sillitin N87, Sillitin N82, Sillitin V85 and Sillitin V88 by Hoffmann Mineral.

They may be fumed silicas.

The fumed silicas can be obtained by high-temperature hydrolysis of a volatile silicon compound in an oxy-hydrogen flame, producing a finely divided silica. This process makes it possible especially to obtain hydrophilic silicas which contain a large number of silanol groups at their surface. It is possible to chemically modify the surface of the said silica via a chemical reaction which brings about a reduction in the number of silanol groups. It is possible especially to substitute silanol groups with hydrophobic groups; a hydrophobic silica is then obtained.

The hydrophobic groups can be:
(a) trimethylsiloxyl groups, which are obtained especially by treating fumed silica in the presence of hexamethyldisilazane. Silicas thus treated are known as "Silica silylate" according to the CTFA (6th Edition, 1995) ;
(b) dimethylsilyloxyl or polydimethylsiloxane groups, which are obtained especially by treating fumed silica in the presence of polydimethylsiloxane or dimethyldichlorosilane. Silicas thus treated are known as "Silica dimethyl silylate" according to the CTFA (6th Edition, 1995).

Silica powders that may more particularly be mentioned include:

the porous silica microspheres sold under the name Silica Beads SB-700 by Miyoshi; Sunsphere® H51, Sunsphere® H33 by Asahi Glass;
the polydimethylsiloxane-coated amorphous silica microspheres sold under the name SA Sunsphere® H33 and SA Sunsphere® H53 by Asahi Glass;
the precipitated silica microspheres, for example coated with inorganic wax such as polyethylene, and sold especially under the name Acematt OK 412 by Evonik Degussa.

A Nylon powder that may be mentioned is the Nylon powder sold under the name Orgasol® 4000 by Atochem.

The silicone elastomers are especially elastomeric partially or completely crosslinked organopolysiloxanes, having a three-dimensional structure, such as those sold under the names KSG6®, KSG16® and KSG18® by SHIN-ETSU, Trefil E-505C® and Trefil E-506C® by DOW-CORNING, Gransil SR-CYC®, SR DMF10®, SR-DC556®, SR 5CYC gel®, SR DMF 10 gel® and SR DC 556 gel® by GRANT INDUSTRIES, SF 1204® and JK 113® by GENERAL ELECTRIC.

Silicone elastomer powders that may be mentioned include the powders sold under the names "Trefil® Powder E-505C" and "Trefil® Powder E-506C" by Dow Corning.

As silicone powder, gum beads of crosslinked polydimethylsiloxane coated with silsesquioxane resin may be mentioned, especially sold under the name KSP100 by Shin Etsu, silicone resin powders in the form of rugby balls such as especially the product sold under the name NLK-602 by TAKEMOTO.

Perlite is a natural glass of volcanic origin, shiny light-grey or black in colour, which results from the rapid cooling of lava and which is provided in the shape of small particles resembling pearls.

The perlite particles used according to the invention are especially commercially available from World Minerals Europe under the trade name Perlite P1430, Perlite P2550 or Perlite P2040. These particles are sold as mattifying agents for paints. They are presented in the form of a white powder having a crystalline silica content below 0.1% by weight.

Preferably, the perlite particles according to the invention have a particle size distribution such that at least 50% of the particles have a size of less than 25 μm, preferably of less than 20 μm. In addition, they preferably have a particle size distribution such that 90% by weight of the particles have a size of less than 55 μm and preferably of less than 40 μm. Furthermore, it is preferable for 90% by weight of the particles to have a size of greater than 5 μm.

Boron nitride particles may be mentioned, such as PUHP1030L by Saint Gobain Ceramics, UHP-1010 by Carborundum, Ronaflair Extender by Merck, Covalumine Atlas White AS by Sensient, Boroneige 601 by ESK, PUHP3008 by Saint Gobain Ceramics.

Clays are products that are already well known per se, which are described, for example, in the publication Minéralogie des argiles [Mineralogy of Clays], S. Caillère, S. Hénin, M. Rautureau, 2nd Edition 1982, Masson.

Clays are silicates containing a cation that may be chosen from calcium, magnesium, aluminium, sodium, potassium and lithium cations, and mixtures thereof.

Examples of such products that may be mentioned include clays of the smectite family such as montmorillonites, hectorites, bentonites, beidellites and saponites, and also of the family of vermiculites, stevensite and chlorites.

The clays can be of natural or synthetic origin. Preferably, clays that are cosmetically compatible and acceptable with keratin fibres such as the hair are used.

The clay can be chosen from montmorillonite, bentonite, hectorite, attapulgite, sepiolite and their mixtures. Preferably, the clay is a bentonite or a hectorite.

The clays may be chosen from organophilic clays.

The organophilic clays are clays modified with a chemical compound chosen from quaternary amines, tertiary amines, amine acetates, imidazolines, amine soaps, fatty sulfates, alkyl aryl sulfonates and amine oxides, and mixtures thereof.

Preferably, the organophilic clays according to the invention are clays modified with a chemical compound chosen from quaternary amines.

Organophilic clays that may be mentioned include quaternium-18 bentonites such as those sold under the names Bentone 3, Bentone 38 and Bentone 38V by Elementis, Tixogel VP by United Catalyst, and Claytone 34, Claytone 40 and Claytone XL by Southern Clay; stearalkonium bentonites such as those sold under the names Bentone 27V by Elementis, Tixogel LG by United Catalyst, and Claytone AF and Claytone APA by Southern Clay and quaternium-18/benzalkonium bentonites such as those sold under the names Claytone HT and Claytone PS by Southern Clay.

The organophilic clay is particularly chosen from modified hectorites such as the hectorite modified by $C_{10}$-$C_{12}$ fatty acid ammonium chloride, especially distearyldimethylammonium chloride and stearylbenzyldimethylammonium chloride.

The clays are especially chosen from montmorillonites and kaolin.

Particularly preferred particles that absorb sebum are silica powders, especially silica powders especially precipitated and more specifically precipitated silicas coated with wax, boron nitride, acrylic polymer powders.

Preferably, the particles have a number-average size of between 50 nm and 350 microns, better still between 100 nm and 100 microns and even more preferentially between 0.5 and 100 microns.

The sebum-absorbing particles may be present in the composition according to the invention in a content ranging from 0.01% to 30% by weight, preferably ranging from 0.1% to 20% by weight and most preferentially ranging from 0.5% to 10% by weight, relative to the total weight of the composition.

Method for Measuring the Sebum Uptake of a Powder:

The sebum uptake of a powder is measured according to the method for determining the oil uptake of a powder as described in standard NF T 30-022. It corresponds to the amount of sebum adsorbed onto the available surface of the powder, by measuring the wet point.

An amount m (in grams) of powder of between about 0.5 g and 5 g (the amount depends on the density of the powder) is placed on a glass plate and artificial sebum having the composition below is then added dropwise:

| | |
|---|---|
| triolein | 29% |
| oleic acid | 28.5% |
| oleyl oleate | 18.5% |
| squalene | 14% |
| cholesterol | 7% |
| cholesteryl palmitate | 3% |

After addition of 4 to 5 drops of artificial sebum, the artificial sebum is incorporated into the powder using a spatula, and the addition of the artificial sebum is continued until conglomerates of artificial sebum and of powder form. From this point, the artificial sebum is added one drop at a time and the mixture is then triturated with the spatula. The addition of artificial sebum is stopped when a firm, smooth paste is obtained. This paste must be able to be spread over the glass plate without cracks or the formation of lumps. The volume Vs (expressed in ml) of artificial sebum used is then noted.

The sebum uptake corresponds to the ratio Vs/m.

The composition according to the invention may be cosmetic and/or dermatological, preferably cosmetic.

The composition according to the invention is generally suitable for topical application to the skin and thus generally comprises a physiologically acceptable medium, i.e. a medium that is compatible with the skin and/or its integuments. It is preferably a cosmetically acceptable medium, i.e. a medium which has a pleasant colour, odour and feel and which does not cause any unacceptable discomfort (stinging, tautness or redness) liable to discourage the consumer from using this composition.

The composition according to the invention may be in any pharmaceutical form conventionally used for a topical application and especially in the form of dispersions of gel or lotion type, emulsions of liquid or semi-liquid consistency of the milk type, obtained by dispersing an oil phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or non-ionic type, or wax/aqueous phase dispersions. The composition according to the invention may as a variant be presented in anhydrous form such as sticks or compact or free powders. These compositions are prepared according to the usual methods.

In addition, the compositions used according to the invention can be more or less fluid and can have the appearance of a white or coloured cream, of an ointment, of a milk, of a lotion, of a serum, of a paste or of a foam. They may optionally be applied to the skin in the form of an aerosol. They can also be in solid form, for example in the form of a stick.

Preferably, the compositions are liquid.

When the composition used according to the invention comprises an oil phase, it preferably contains at least one oil. It may also contain other fatty substances.

Mention may be made, as oils which can be used in the composition of the invention, for example, of:

hydrocarbon oils of animal origin, such as perhydrosqualene;

hydrocarbon oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by Stearineries Dubois or those sold under the names Miglyol 810, 812 and 818 by Dynamit Nobel, jojoba oil and shea butter oil;

synthetic esters and ethers, especially of fatty acids, for instance the oils of formulae $R_1COOR_2$ and $R_1OR_2$ in which $R_1$ represents a fatty acid residue containing from 8 to 29 carbon atoms and $R_2$ represents a branched or unbranched hydrocarbon-based chain containing from 3 to 30 carbon atoms, for instance Purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate;

straight or branched hydrocarbons of inorganic or synthetic origin, such as volatile or non-volatile liquid paraffins, and derivatives thereof, petroleum jelly, polydecenes, and hydrogenated polyisobutene such as Parleam oil;

fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils, for instance those described in document JP-A-2-295 912;

silicone oils, for instance volatile or non-volatile polymethylsiloxanes (PDMSs) with a straight or cyclic silicone chain, which are liquid or pasty at room temperature, especially cyclopolydimethylsiloxanes (cyclomethicones) such as cyclohexasiloxane; polydimethylsiloxanes containing alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;

mixtures thereof.

In the list of the abovementioned oils, the term "hydrocarbon oil" is understood to mean any oil predominantly containing carbon and hydrogen atoms, and optionally ester, ether, fluoro, carboxylic acid and/or alcohol groups.

The other fatty substances that may be present in the oil phase are, for example, fatty acids containing from 8 to 30 carbon atoms, for instance stearic acid, lauric acid, palmitic acid and oleic acid; waxes, for instance lanolin wax, beeswax, carnauba wax or candelilla wax, paraffin wax, lignite wax or microcrystalline waxes, ceresin or ozokerite, and synthetic waxes, for instance polyethylene waxes and Fischer-Tropsch waxes; silicone resins such as trifluoromethyl-$C_{1-4}$-alkyl dimethicone and trifluoropropyl dimethicone; and silicone elastomers, for instance the products sold under the name KSG by Shin-Etsu, under the name Trefil, BY29 or EPSX by Dow Corning, or under the name Gransil by Grant Industries.

These fatty substances can be chosen in a varied manner by those skilled in the art so as to prepare a composition having the desired properties, for example of consistency or texture.

According to one particular embodiment of the invention, the composition according to the invention is a water-in-oil (W/O) or oil-in-water (O/W) emulsion, preferably an O/W emulsion.

The O/W emulsion also comprises emulsified gels. The term "emulsified gels" means dispersions of oils in an aqueous gel. The addition of surfactant is optional for this pharmaceutical form.

The proportion of the oil phase of the emulsion may range from 2% to 80% by weight and preferably from 5% to 50% by weight relative to the total weight of the composition.

The emulsions generally contain at least one emulsifier chosen from amphoteric, anionic, cationic or non-ionic emulsifiers, used alone or as a mixture, and optionally a co-emulsifier. The emulsifiers are appropriately chosen according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol sold under the name DC 5225 C by Dow Corning, and alkyl dimethicone copolyols such as the lauryl methicone copolyol sold under the name Dow Corning 5200 Formulation Aid by Dow Corning, and the cetyl dimethicone copolyol sold under the name Abil EM 90® by Goldschmidt. A crosslinked elastomeric solid organopolysiloxane containing at least one oxyalkylenated group, such as those obtained according to the procedure of Examples 3, 4 and 8 of document U.S. Pat. No. 5,412,004 and of the examples of document U.S. Pat. No. 5,811,487, especially the product of Example 3 (synthesis example) of patent U.S. Pat. No.

5,412,004, such as the product sold under the reference KSG 21 by Shin-Etsu, may also be used as surfactant for W/O emulsions.

For O/W emulsions, examples of emulsifiers that may be mentioned include non-ionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

The composition may be an aqueous gel, and may especially comprise common aqueous gelling agents.

Advantageously, the composition is a composition comprising at least one aqueous phase. The aqueous phase generally represents more than 5% by weight of the total weight of the composition and preferably more than 20% by weight.

The composition according to the invention comprises an aqueous phase comprising water and optionally glycols, ethanol and/or hydrophilic adjuvants, which may be water-soluble at room temperature. The composition generally comprises from 30 to 95% water.

Advantageously, the composition according to the invention has a pH ranging from 3 to 8. Preferably, the pH of the composition ranges from 4 to 6.

The composition according to the invention may be a composition for caring for, cleansing or making up bodily or facial skin, in particular a care composition.

The skincare composition may be, for example, a facial cream, gel or fluid.

The skin makeup composition may be, for example, a foundation, an eyeshadow, a face powder, a concealer product, a face and body powder, or a body makeup product.

Additives:

The composition according to the present invention may also contain various adjuvants commonly used in cosmetics, such as emulsifiers; fillers; preserving agents; sequestrants; dyes; fragrances; thickeners and gelling agents, in particular acrylamide homopolymers and copolymers, acrylic homopolymers and copolymers and acrylamidomethylpropanesulfonic acid (AMPS®) homopolymers and copolymers; UV-screening agents.

Advantageously, to reinforce the mattifying effects of the composition according to the invention, it also comprises at least one active agent for caring for oily skin. This active agent is preferentially chosen from desquamating agents, antimicrobial agents, anti-inflammatory agents, sebum regulators and antioxidants.

It may also contain cosmetic active agents other than those for caring for oily skin, for instance moisturizers and vitamins.

Naturally, a person skilled in the art will take care to select this or these optional additional compound(s), and/or the amount thereof, such that the advantageous properties of the composition according to the invention are not, or are not substantially, adversely affected by the envisaged addition.

Active Agent for Caring for Oily Skin

In the context of the present invention, the expression "active agent for caring for oily skin" is understood to mean a compound which intrinsically has—i.e. not requiring the intervention of an external agent to activate it—biological activity which may be in particular:

desquamating activity (which allows the opening of the comedones), and/or antimicrobial activity (especially on *P. acnes*), and/or anti-inflammatory activity, and/or sebum-regulating activity, and/or antioxidant activity (which prevents the oxidation of squalene and the formation of comedones).

The active agent for caring for oily skin may thus be chosen from: desquamating agents and/or antimicrobial agents and/or anti-inflammatory agents and/or sebum regulators and/or antioxidants.

1. Desquamating Agents

The term "desquamating agent" means any compound capable of acting:

either directly on desquamation by promoting exfoliation, such as β-hydroxy acids, in particular salicylic acid and derivatives thereof (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; resveratrol and certain jasmonic acid derivatives;

or on the enzymes involved in desquamation or decomposition of the corneodesmosomes, such as glycosidases, stratum corneum chymotryptic enzyme (SCCE) or indeed even other proteases (trypsin, chymotrypsin-like). Mention may be made of aminosulfonic compounds and in particular N-(2-hydroxyethyl)piperazine-N-2-ethanesulfonic acid (HEPES); 2-oxothiazolidine-4-carboxylic acid (procysteine) derivatives; derivatives of α-amino acids of glycine type (as described in EP-0 852 949, and also sodium methyl glycine diacetate sold by BASF under the trade name Trilon M); honey; sugar derivatives such as O-octanoyl-6-D-maltose and N-acetylglucosamine.

5-n-Octanoylsalicylic acid is preferred for use in the present invention.

2. Antimicrobial Agents

The antimicrobial agents that may be used in the composition according to the invention may especially be chosen from 2,4,4'-trichloro-2'-hydroxydiphenyl ether (or triclosan), 3,4,4'-trichlorocarbanilide, phenoxyethanol, phenoxypropanol, phenoxyisopropanol, hexamidine isethionate, metronidazole and salts thereof, miconazole and salts thereof, itraconazole, terconazole, econazole, ketoconazole, saperconazole, fluconazole, clotrimazole, butoconazole, oxiconazole, sulfaconazole, sulconazole, terbinafine, ciclopirox, ciclopirox olamine, undecylenic acid and salts thereof, benzoyl peroxide, 3-hydroxybenzoic acid, 4-hydroxybenzoic acid, phytic acid, N-acetyl-L-cysteine acid, lipoic acid, azelaic acid and salts thereof, arachidonic acid, resorcinol, 2,4,4'-trichloro-2'-hydroxydiphenyl ether, 3,4,4'-trichlorocarbanilide, octopirox, octoxyglycerine, octanoylglycine, caprylyl glycol, 10-hydroxy-2-decanoic acid, dichlorophenylimidazoledioxolane and derivatives thereof described in patent WO 93/18743, copper pidolate, salicylic acid, zinc salicylate, iodopropynyl butylcarbamate, farnesol and phytosphingosines, and mixtures thereof.

The preferred antimicrobial agents are octoxyglycerine, copper pidolate, zinc salicylate, salicylic acid and iodopropynyl butylcarbamate.

3. Anti-Inflammatory Agents

As anti-inflammatory or soothing agents that may be used in the composition according to the invention, mention may be made of: pentacyclic triterpenes and plant extracts (e.g.: *Glycyrrhiza glabra*) containing the same, for instance β-glycyrrhetinic acid and salts and/or derivatives thereof (glycyrrhetinic acid monoglucuronide, stearyl glycyrrhetinate, 3-stearoyloxyglycyrrhetic acid), ursolic acid and salts thereof, oleanolic acid and salts thereof, betulinic acid and salts thereof, bisabolol, an extract of *Paeonia suffruticosa* and/or *lactiflora*, salicylic acid salts and in particular zinc salicylate, phycosaccharides from the company Codif, an extract of *Laminaria saccharina*, canola oil, bisabolol and extracts of camomile, allantoin, Sepivital EPC (phosphoric diester of vitamins E and C) from Seppic, omega-3 unsaturated oils such as musk rose oil, blackcurrant oil, ecchium oil, fish oil, plankton extracts, capryloyl glycine, Seppicalm VG (sodium palmitoylproline and *Nymphaea alba*) from Seppic, an extract of *Pygeum*, an extract of *Boswellia serrata*, an extract of *Centipeda cunninghami*, an extract of *Helianthus annuus*, an extract of *Linum usitatissimum*, tocotrienols, extracts of *Cola nitida*, extracts of *Centella asiatica*, piperonal, an extract of clove, an extract of *Epilobium angustifolium*, aloe vera, an extract of *Bacopa monieri*, phytosterols, niacinamide, cortisone, hydrocortisone, indomethacin and betamethasone.

The preferred anti-inflammatory agents for use in the present invention are extracts of *Centella asiatica*, β-glycyrrhetinic acid and salts thereof, α-bisabolol and niacinamide.

4. Sebum Regulators

When the composition according to the invention comprises a sebum regulator such as a 5α-reductase inhibitor, this agent may be chosen especially from:
retinoids, and in particular retinol;
sulfur and sulfur derivatives;
zinc salts such as zinc lactate, gluconate, pidolate, carboxylate, salicylate and/or cysteate;
selenium chloride;
vitamin B6 or pyridoxine;
the mixture of capryloyl glycine, sarcosine and *Cinnamomum zeylanicum* extract sold especially by Seppic under the trade name Sepicontrol A5®;
an extract of Laminaria saccharina sold especially by Secma under the trade name Phlorogine®;
an extract of *Spiraea u/maria* sold especially by Silab under the trade name Sebonormine®;
extracts of plants of the species *Arnica montana, Cinchona succirubra, Eugenia caryophyllata, Humulus lupulus, Hypericum perforatum, Mentha piperita, Rosmarinus officinalis, Salvia officinalis* and *Thymus vulgaris*, all sold, for example, by Maruzen;
an extract of *Serenoa repens* sold especially by Euromed;
extracts of plants of the genus *Silybum*;
plant extracts containing sapogenins and in particular extracts of *Dioscorea* plants rich in diosgenin; and
extracts of *Eugenia caryophyllata* containing eugenol and eugenyl glucoside.

Zinc salts are preferred for use in the present invention.

5. Antioxidants

The antioxidants that are preferred for use in the present invention may be chosen from tocopherol and esters thereof, such as tocopheryl acetate; BHT and BHA.

The active agent(s) used in the composition according to the invention may represent from 0.01% to 50%, preferably from 0.1% to 25% and better still from 0.5% to 10% of the total weight of the composition.

The invention also relates to a cosmetic process for caring for and/or making up the skin, comprising the topical application to the skin of the composition according to the invention.

More precisely, it is a process for making the skin matt and/or for reducing its shine.

The term "mattifying" means making the skin more matt and reducing its shine, and thus its unattractive reflections.

The invention also relates to the cosmetic use of the composition according to the invention for caring for combination skin and/or oily skin.

The invention will now be illustrated with the aid of the non-limiting examples that follow. In these examples, the amounts are indicated as weight percentages. Depending on the case, the compounds are mentioned using chemical names or using CTFA names (International Cosmetic Ingredient Dictionary and Handbook).

EXAMPLES

Example 1

A facial-care cream in the form of an oil/water emulsion having the composition below was prepared:

| INCI name (EU) | In weight % |
|---|---|
| STEARYL ALCOHOL | 0.7 |
| GLYCERYL STEARATE | 1 |
| POLYACRYLAMIDE (Sepigel 305 by Seppic) | 0.25 |
| GLYCERINE | 7 |
| ISONONYL ISONONANOATE | 5 |
| DIMETHICONE | 5 |
| CETEARYL ALCOHOL | 2.5 |
| Water | Qs for 100 |
| CAPRYLOYL SALICYLIC ACID | 0.11 |
| GLYCERYL STEARATE | 3 |
| OLETH-10 | 1 |
| PEG-100 STEARATE | 1 |

In this base, the same combinations of fillers according to the invention were used as below.

This composition may be applied in the morning and/or evening to the face to make combination skin and oily skin matt.

Example 2

Measuring Mattness/Shine

Base Formula

| In % AM | |
|---|---|
| Isopropyl N-lauroylsarcosinate (Eldew SL 205 from Ajinomoto) | 5 |
| Triblock copolymer of ethylene oxide, propylene oxide and ethylene oxide (128 EO/54 PO/128 EO) (Synperonic PE/F 108 from Croda) | 1 |
| Glycerol | 5 |
| Ammonium polyacryldimethyltauramide (Hostacerin AMPS ® from Clariant) | 1.56 |
| Phenoxyethanol | 0.3 |
| Hexyl laurate | 5 |
| Caprylyl glycol | 0.3 |
| Xanthan gum | 0.1 |
| Water qs for | 100 |

In this base, the contents of the 3 fillers are varied between 0 and 0.5%. The total filler content remains constant (0.5%).

Then the mattness of the formula after application is measured (immediately and in the long term).

Examples for a total filler content of 0.5%

|  | Content | Mattness performance |
|---|---|---|
| Fillers | | |
| Silica silylate (VM-2270 Aerogel Fine Particles from Dow Corning) | 0.5 | + |
| Ethylene glycol dimethacrylate/lauryl methacrylate copolymer (Polytrap 6603 Adsorber) | 0.5 | + |
| Perlite | 0.5 | + |
| Silicone elastomer (KSG 16) | 0.5 | 0 |
| Silica (Acematt OK 412) | 0.5 | 0 |
| Combinations | | |
| Aerogel-Silicone elastomer | 0.25%-0.25% | + |
| Aerogel-Silicone elastomer-Polytrap | 0.17%-0.17%-0.17% | +++ |
| Aerogel-Silicone elastomer-Silica | 0.17%-0.17%-0.17% | +++ |
| Aerogel-Silicone elastomer-Perlite | 0.17%-0.17%-0.17% | +++ |
| Aerogel-Silicone elastomer-Expancel | 0.17%-0.17%-0.17% | +++ |

Measuring Mattness by In Vitro Assessment

The mattness obtained with composition A according to the invention, and with composition B given as a comparison example, is measured by using a contrast card (Prufkarte type 24/5-250 cm$^2$) sold by Erichsen. The composition has been spread at 2 mg/cm$^2$ using a mechanical film-stretcher. A mixture was sprayed 10 times (water/sebum 80/20), then there was a 6-minute wait at room temperature, then reflection was measured using a gonioreflectometer. The result obtained is the ratio R between the specular reflection and the diffuse reflection. The value of R is proportionately smaller the greater the mattifying effect.

−: shine
0: no effect
+: matt
++: matt+
+++: very matt

These results show that the composition according to the invention delivers skin shine less than that obtained by a composition containing each of the particles taken in isolation at the same total concentration.

The invention claimed is:

1. A cosmetic and/or dermatological composition comprising, in a physiologically acceptable medium:
a sebum absorbing component consisting of:
a) from 0.5% to 5% by weight relative to the total weight of the composition of hydrophobic silica aerogel particles,
b) from 0.20% to 5% by weight relative to the total weight of the composition of non-emulsifying silicone elastomer particles different than the particles c), and
c) from 0.5% to 10% by weight relative to the total weight of the composition of particles that absorb sebum different than the particles a) and b) and being chosen from silica powders, and powders of acrylic polymers, and mixtures thereof, and wherein the said composition also comprises at least one aqueous phase.

2. The cosmetic composition according to claim 1, in which the hydrophobic silica aerogel particles have a specific surface area per unit of mass ranging from 200 to 1500 m$^2$/g.

3. The cosmetic composition according to claim 1, in which the hydrophobic silica aerogel particles have a specific surface area per unit of mass ranging from 600 to 1200 m$^2$/g.

4. The cosmetic composition according to claim 1, in which the hydrophobic silica aerogel particles have a size, expressed as the volume-mean diameter, ranging from 5 to 25 μm.

5. The cosmetic composition according to claim 1, in which the hydrophobic silica aerogel particles have a tapped density ranging from 0.02 g/cm$^3$ to 0.10 g/cm$^3$.

6. The cosmetic composition according to claim 1, in which the hydrophobic silica aerogel particles have a specific surface area per unit of volume ranging from 5 to 60 m$^2$/cm$^3$.

7. The cosmetic composition according to claim 1, in which the hydrophobic silica aerogel particles have an oil-absorbing capacity, measured at the wet point, ranging from 5 to 18 ml/g.

8. The cosmetic composition according to claim 1, in which the hydrophobic silica aerogel particles are inorganic particles.

9. The cosmetic composition according to claim 1, wherein the silicone elastomer particles are obtained by polymerization of organopolysiloxane having at least two hydrogen atoms each bound to a silicon atom and of an organopolysiloxane comprising at least two ethylenically unsaturated groups in the presence of a platinum catalyst.

10. The cosmetic composition according to claim 1, which also comprises at least one active agent for caring for oily skin chosen from desquamating agents, antimicrobial agents, anti-inflammatory agents, sebum regulators and antioxidants.

11. The cosmetic composition according to claim 2, in which the hydrophobic silica aerogel particles have a specific surface area per unit of mass ranging from 600 to 1200 m$^2$/g.

12. The cosmetic composition according to claim 2, in which the hydrophobic silica aerogel particles have a size, expressed as the volume-mean diameter, ranging from 5 to 25 μm.

13. The cosmetic composition according to claim 1, wherein the particles that absorbs sebum different than the particles a) and b) are chosen from silica powders.

* * * * *